United States Patent
Parikh et al.

(10) Patent No.: US 8,779,000 B1
(45) Date of Patent: Jul. 15, 2014

(54) SACCHARIDE FREE, STORAGE STABLE THYROID HORMONE ACTIVE DRUG FORMULATIONS AND METHODS FOR THEIR PRODUCTION

(71) Applicants: Nilesh Parikh, Irvine, CA (US); William Hite, Winchester, CA (US)

(72) Inventors: Nilesh Parikh, Irvine, CA (US); William Hite, Winchester, CA (US)

(*) Notice: Subject to any disclaimer, the term of this patent is extended or adjusted under 35 U.S.C. 154(b) by 0 days.

(21) Appl. No.: 13/947,022

(22) Filed: Jul. 20, 2013

(51) Int. Cl.
*A61K 31/195* (2006.01)
*A61K 9/20* (2006.01)
*A61K 9/14* (2006.01)
*A61K 47/00* (2006.01)
*A61K 47/06* (2006.01)

(52) U.S. Cl.
USPC ........... 514/567; 424/400; 424/464; 424/465; 424/468; 424/489; 424/499; 424/502

(58) Field of Classification Search
USPC .......... 514/567; 424/400, 464, 465, 468, 489, 424/499, 502
See application file for complete search history.

(56) References Cited

U.S. PATENT DOCUMENTS

| | | | | |
|---|---|---|---|---|
| 5,225,204 | A * | 7/1993 | Chen et al. | 424/484 |
| 5,955,105 | A * | 9/1999 | Mitra et al. | 424/464 |
| 6,645,526 | B2 * | 11/2003 | Hanshew et al. | 424/465 |
| 7,052,717 | B2 * | 5/2006 | Hanshew et al. | 424/464 |
| 7,195,779 | B2 * | 3/2007 | Hanshew et al. | 424/465 |

* cited by examiner

*Primary Examiner* — Raymond Henley, III

(57) ABSTRACT

Embodiments of the present invention provide pharmaceutical compositions in unit dosage form that comprise a therapeutically effective amount of levothyroxine sodium; an antioxidant in an amount sufficient to stabilize the levothyroxine sodium against oxidation; an amount of an alditol sufficient to stabilize the levothyroxine sodium; and at least two excipients selected from a filler, a binder, and a lubricant. Such compositions are free of added monosaccharide, disaccharide, and an oligosaccharide and are storage stable.

23 Claims, No Drawings

SACCHARIDE FREE, STORAGE STABLE THYROID HORMONE ACTIVE DRUG FORMULATIONS AND METHODS FOR THEIR PRODUCTION

FIELD OF THE INVENTIONS

Embodiments of the invention relate to methods of preparing saccharide-free, storage-stable pharmaceutical compositions of thyroid hormone and compositions made by these methods.

BACKGROUND OF THE INVENTIONS

Thyroid hormone active drugs are known for both therapeutic and prophylactic treatment of thyroid disorders. For example, levothyroxine sodium is prescribed for thyroid hormone replacement therapy in cases of reduced or absent thyroid function in ailments such as myxedema, cretinism, and obesity. See, for example, Post and Warren in *Analytical Profiles of Drug Substances*, Vol. 5, Florey (ed.); Academic Press, New York (1976), pp. 226-281. Levothyroxine sodium is quite unstable, hygroscopic and degrades rapidly when subjected to high humidity, light or high temperature. See, for example, Won, *Pharm. Res.*9(1):131-137, 1992. Because of the physico-chemico properties of the drug, many levothyroxine sodium formulations have short stability duration, worsened under conditions of high humidity and temperature. Tablets may decompose approximately 1 percent per month. Gupta et. al., *J. Clin. Pharm. Ther.* 15:331-335, 1990. The stability problem has been so widespread that some drug companies marketing levothyroxine sodium tablets have been forced to recall various batches due to lack of stability.

Formulations containing levothyroxine sodium have been known since the late 1950s. There have been attempts to develop more stable dosage formulations of levothyroxine sodium. For example, U.S. Pat. No. 5,635,209 discloses levothyroxine sodium in combination with potassium iodide as part of a stabilizing excipient. In the manufacture of this formulation, levothyroxine sodium was first mixed with microcrystalline cellulose, and then added to a dried granulation of potassium iodide and microcrystalline cellulose. The formulation purportedly provided increased active drug potency over a three month period in comparison to then commercially available formulations.

U.S. Pat. No. 5,225,204 teaches a complex of levothyroxine sodium and a cellulose, polyvinylpyrrolidone or poloxamer. The formulation may be prepared by dissolving the drug complex in a polar organic solvent, adding a cellulose carrier to the liquid, and drying the resulting mixture to obtain a complex of levothyroxine sodium and polyvinylpyrrolidone or poloxamer adsorbed on the cellulose carrier. Tests of such combinations yielded stability results at best equal to commercially available preparations such as those described in U.S. Pat. No. 5,955,105, and in some cases substantially worse. The inventors of this stabilized composition teach one of skill in the art away from the use of carbohydrates in levothyroxine sodium formulations, stating that instability of the dosage form was the result of an interaction between the active drug substance and carbohydrate excipients.

U.S. Pat. No. 5,955,105 teaches that levothyroxine is relatively stable in pure form and that the instability of levothyroxine is due to its interaction with particular excipients. The patent teaches that thyroid hormones, particularly levothyroxine sodium, are compatible with carbohydrates, such as starch and maltodextrin, but incompatible with lactose, glucose and sucrose. The patent teaches a formula for direct compression levothyroxine sodium dosage forms that contains a soluble polysaccharide, designed to eliminate the interaction between the drug and other excipients, and carbohydrate having a molecular weight greater than 500.

U.S. Pat. Nos. 7,195,779 and 7,052,717 teach storage-stable pharmaceutical compositions of thyroid hormones, such as levothyroxine sodium, are achieved by blending the active ingredient with stabilizing amounts of mannitol and sucrose, or mannitol, sucrose, and antioxidant butylated hydroxyanisole (BHA), to form a granulation intermediate. The patents teach that a stabilizing effect is achieved for levothyroxine sodium in its formulations due to the presence of the mannitol and sucrose, or mannitol, sucrose, and BHA, both at an early stage of manufacture and in the final dosage form.

SUMMARY OF THE INVENTIONS

Embodiments of the present invention provide pharmaceutical compositions in unit dosage form that comprise a therapeutically effective amount of levothyroxine sodium; an antioxidant in an amount sufficient to stabilize the levothyroxine sodium against oxidation; an amount of an alditol sufficient to stabilize the levothyroxine sodium; and two or more of a filler, a binder, and a lubricant. Such compositions are free of added monosaccharide, disaccharide, and an oligosaccharide and storage stable.

In some embodiments, the filler is one or more of a calcium phosphate, a cellulose, a magnesium carbonate, a calcium carbonate, and a calcium sulfate.

In some embodiments, the binder is one or more of a polyvinylpyrrolidone, an alginate, a gelatin, a chitosan, a kaolin, an acacia, a methyl cellulose, a liquid glucose tragacanth, a starch, a starch paste, a pregelatinized starch, an ethyl cellulose, a hydroxypropylmethyl cellulose, a hydroxypropyl cellulose, a sodium carboxymethyl cellulose, an alginic acid, a polyvinyl pyrrolidone, a cellulose, a polyethylene glycol, a polyvinyl alcohol, and a polymethacrylate.

In some embodiments, the lubricant is one or more of a talc, a calcium stearate, a sodium stearyl fumarate, a stearic acid, a magnesium stearate, a solid polyethylene glycol, a cocoa butter, a hydrogenated vegetable oil, a mineral oil, a glyceryl palmitostearate, and a glyceryl behenate.

In some embodiments, the antioxidant is one or more of a butylated hydroxyanisole (BHA), a vitamin E (alpha tocopherol), a butylated hydroxytoluene (BHA), an ascorbic acid, a sodium ascorbate, a sodium bisulfate, and a sodium metabisulfite.

In some embodiments, the composition further comprises one or more of a glidant and a surfactant. In some embodiments, the glidant is one or more of a talc, a silica, a fumed silica, and a colloidal silicon dioxide. In some embodiments, the surfactant is one or more of a polysorbate, a sodium lauryl sulfate, a lauryl dimethyl amine oxide, a cetyltrimethylammonium bromide, a polyethoxylated alcohol, a polyoxyethylene sorbitan, an octoxynol, a n,n-dimethyldodecylamine-n-oxide, a hexadecyltrimethylammonium bromide, a polyoxyl 10 lauryl ether, a BRIJ 721, a bile salt, a polyoxyl castor oil, a nonylphenol ethoxylate, a cyclodextrin, a lecithin, and a methylbenzethonium chloride.

DETAILED DESCRIPTION OF THE INVENTIONS

The prior art teaches that the combination of alditol and mono-, di-, or oligo-saccharide, or alditol, mono-, di-, or oligo-saccharide, and BHA, provides stable granulation intermediates of levothyroxine, to which additional excipients may be added to form unit dosage form oral pharmaceutical compositions that maintain a predictable dosage of active levothyroxine for a substantial period of time. The compositions of the present invention comprise a thyroid hormone and an alditol and BHA in the absence of added monosaccharide, disaccharide, and oligosaccharide. The unit dosage form oral pharmaceutical compositions of the invention have unexpectedly excellent storage-stability properties. Accordingly, the invention provides a stable dosage form in which the dosage of thyroxine active drug, such as levothyroxine sodium, is surprisingly maintained at a predictable level for a substantial period of time.

In some embodiments, methods of making the unit dosage form oral pharmaceutical compositions of the invention include a granulation intermediate containing the thyroxine active drug substance, BHA and an alditol, to which pharmaceutically acceptable excipients are added. This invention can be used to produce stable formulations of any natural or synthetic thyroid hormone replacement drug. Therefore, although the following description and examples refer to compositions and methods using levothyroxine sodium, the hormone embodiments of the invention encompass other thyroid hormone medications of the general formula I:

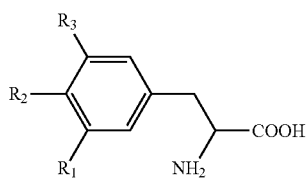

I wherein $R_1$ and $R_3$ may be the same or different and are selected from hydrogen; halogen; alkyl; aryl; cycloalkyl; heterocycloalkyl; amide; alcohol; acid; ester; ether; acyl; alkenyl; and alkynyl; wherein $R_2$ is

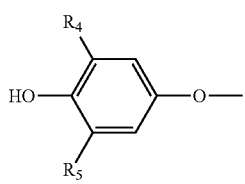

wherein $R_4$ and $R_5$ may be the same or different and are selected from hydrogen; halogen; alkyl; aryl; cycloalkyl; heterocycloalkyl; amide; alcohol; acid; ester; ether; acyl; alkenyl; and alkynyl. The medication can be in the form of a free acid, a free base, an organic salt, an inorganic salt, or a hydrate. Liothyronine is an example of a drug encompassed by the above-mentioned general formula.

In certain embodiments, stabilized pharmaceutical compositions are produced by blending the active ingredient with an alditol and granulating with an antioxidant to form a granulation intermediate. Further pharmaceutical excipients are generally added to produce final oral dosage forms, such as tablets, capsules, powders, or sachets, though such addition is optional. Useful granulation solvents include water and ethanol.

In certain embodiments, antioxidants that have low water solubility, such as BHA or BHT, may be added to a solvent in which they are reasonably soluble, such as alcohol, glycerin, and propylene glycol, and then used in preparing a granulation intermediate. In some embodiments, water may be added to such a water-insoluble, antioxidant-solvent solution to form a solution (e.g., about 10-90% water) for use in preparing a granulation intermediate.

In certain embodiments, formulations according to the present invention are made according to the following general steps. The active thyroxine ingredient (e.g., levothyroxine sodium) is blended with an alditol to form a pre-blend. Granulation intermediates are produced by making a wet granulation of the active ingredient with an alditol (e.g., mannitol) and a granulation aid (e.g., microcrystalline cellulose). One or both of the pre-blend or the solution used for preparing the granulation intermediate additionally include(s) an antioxidant, such as BHA or BHT. The levothyroxine sodium is thus blended first with the alditol, and then further excipients (e.g., microcrystalline cellulose or polyvinylpyrrolidone as binder) may be incorporated into the granulation, but need not be added until the active ingredient is intimately mixed with the alditol. Therefore, the microcrystalline cellulose or other diluent functions as a granulation aid and compression enhancer (for tablet or capsule formulations) and not as a specific carrier for the thyroxine active drug.

In some embodiments, the wet granulation is dried, milled and optionally further blended. The granulation intermediate then may be stored or directly mixed with further ingredients to form a composition suitable for compression into tablets, filling into capsules or sachets, or dissolved or suspended to form a liquid dosage form.

Alditols for use in this invention are those whose presence stabilizes the thyroxine drug. Such alditols include one or more of the following: mannitol, sorbitol, maltitol and xylitol. The most preferred alditol is mannitol.

Pharmaceutical compositions of the invention may be prepared for administration orally, rectally, vaginally, transmucosally, transdermally, parenterally, subcutaneously, and intramuscularly. Pharmaceutically acceptable excipients suitable for use in such compositions include, but are not limited to adjuvants, preservatives, buffers, antioxidants, fillers, extenders, carriers, binders, diluents, disintegrants, glidants, lubricants, surfactants, wetting agents, surface active agents, suspending agents, and solvents. Compounds such as dyes, colorants, sweeteners, flavorings, perfuming agents, and taste-masking agents also may be included in formulations according to this invention. In addition, other active ingredients may be included to produce a dual or multiple ingredient medication.

Exemplary disintegrants may be selected from known pharmaceutical excipients such as, for example, crospovidone, crosscarmelose sodium, sodium starch glycolate, partially gelatinized startches, and polacrilin potassium.

Exemplary surfactants may be selected from known pharmaceutical excipients such as, for example, lecithin, stearic acid or other fatty acids, polysorbates, sodium dodecyl sulfate (sodium lauryl sulfate), lauryl dimethyl amine oxide, cetyltrimethylammonium bromide, polyethoxylated alcohols, polyoxyethylene sorbitan, octoxynol (TRITON X100™), n,n-dimethyldodecylamine-n-oxide, hexadecyltrimethylammonium bromide (HTAB), polyoxyl 10 lauryl ether, BRIJ 721 bile salts (e.g., sodium deoxycholate, sodium cholate), polyoxyl castor oil (CREMOPHOR™), nonylphenol ethoxylate (TERGITOL™), cyclodextrins, lecithin, and methylbenzethonium chloride (HYAMINE™).

Exemplary lubricants and/or glidants may be selected from known pharmaceutical excipients such as, for example, talc, calcium stearate, sodium stearyl fumarate, stearic acid, magnesium stearate, solid polyethylene glycols, cocoa butter, hydrogenated vegetable oil, mineral oil, sodium lauryl sulfate, glyceryl palmitostearate, glyceryl behenate, silica, fumed silica, and colloidal silicon dioxide.

Exemplary binders and/or fillers may be selected from known pharmaceutical excipients such as, for example, polyvinylpyrrolidone, sodium citrate, dicalcium phosphate, alkaline inorganic salts, alginates, gelatins, microcrystalline cellulose, chitosan, kaolin, magnesium carbonate, calcium carbonate, acacia, methyl cellulose, liquid glucose tragacanth, ethyl cellulose, gelatin, hydroxypropylmethyl cellulose (HPMC), starch paste, hydroxypropyl cellulose, starch, starch paste, pregelatinized starch, sodium carboxymethyl cellulose, alginic acid, polyvinyl pyrrolidone (PVP), cellulose, polyethylene glycol (PEG), polyvinyl alcohols, and polymethacrylates.

Solid dosage forms which may be prepared according to this invention include tablets, capsules, rectal or vaginal suppositories, pills, dragees, lozenges, granules, beads, microspheres, pellets and powders, or any combination thereof.

The preferred active ingredient in the formulations of this invention is levothyroxine sodium. Therapeutically effective dosage amounts for this drug generally range from about 0.1 µg to about 5000 µg and are most preferably from about 25 µg to about 300 µg. Exemplary dosages therefore include, but are not limited to 20 µg, 25 µg, 50 µg, 75 µg, 88 µg, 100 µg, 112 µg, 125 µg, 150 µg, 175 µg, 200 µg and 300 µg.

Alditol percentages, by weight of dosage form include, but are not limited to, from about 1% to about 90%, such as about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, and ranges therebetween.

Antioxidant percentages, by weight of dosage form include, but are not limited to, from about 0.001% to about 5%, such as about 0.001%, about 0.005%, about 0.01%, about 0.05%, about 0.1%, about 0.5%, about 1%, about 1.5%, about 2%, about 2.5%, about 3%, about 3.5%, about 4%, about 4.5%, about 5%, and ranges therebetween.

Binder percentages, by weight of dosage form include, but are not limited to, from about 0.001% to about 10% such as about 0.001%, about 0.005%, about 0.01%, about 0.05%, about 0.1%, about 0.5%, about 1%, about 1.5%, about 2%, about 2.5%, about 3%, about 3.5%, about 4%, about 4.5%, about 5%, about 6%, about 7%, about 8%, about 9%, about 10% and ranges therebetween.

Glidant percentages, by weight of dosage form include, but are not limited to, from about 0.1% to about 10% such as about 0.1%, about 0.5%, about 1%, about 1.5%, about 2%, about 2.5%, about 3%, about 3.5%, about 4%, about 4.5%, about 5%, about 6%, about 7%, about 8%, about 9%, about 10% and ranges therebetween.

Surfactant percentages, by weight of dosage form include, but are not limited to, from about 0.001% to about 5%, such as about 0.001%, about 0.005%, about 0.01%, about 0.05%, about 0.1%, about 0.5%, about 1%, about 1.5%, about 2%, about 2.5%, about 3%, about 3.5%, about 4%, about 4.5%, about 5%, and ranges therebetween.

Lubricant percentages, by weight of dosage form include, but are not limited to, from about 0.01% to about 10% such as about 0.01%, about 0.05%, about 0.1%, about 0.5%, about 1%, about 1.5%, about 2%, about 2.5%, about 3%, about 3.5%, about 4%, about 4.5%, about 5%, about 6%, about 7%, about 8%, about 9%, about 10% and ranges therebetween.

Disintegrant percentages, by weight of dosage form include, but are not limited to, from about 0.01% to about 10% such as about 0.01%, about 0.05%, about 0.1%, about 0.5%, about 1%, about 1.5%, about 2%, about 2.5%, about 3%, about 3.5%, about 4%, about 4.5%, about 5%, about 6%, about 7%, about 8%, about 9%, about 10% and ranges therebetween.

After the solid ingredients of the formulation are blended, the stabilized drug preparation preferably is compressed into tablets. Alternatively, the preparation may be used to fill capsules such as hard gelatin capsules or used to prepare any other convenient solid dosage form. Compositions according to the invention may be stored in the form of powders, granulates, intermediates, suspensions, or solutions prior to addition of additional desired pharmaceutical excipients for the production of final dosage forms such as tablets or solid-filled capsules, or final liquid dosage forms such as solutions, syrups, suspensions, emulsions and the like.

The following examples further illustrate the invention and are not to be construed to limit the claims in any manner.

EXAMPLE 1

TABLE 1

| Component | Amount in Grams |
| --- | --- |
| Levothyroxine 25 µg tablets were prepared using the following ingredients 0.0334% levothyroxine sodium granulation intermediate | |
| Levothyroxine sodium (anhydrous basis) | 0.10 |
| Mannitol | 202.60 |
| Microcrystalline cellulose | 91.23 |
| Polyvinylpyrrolidone K30 | 6.00 |
| Butylated hydroxyanisole | 0.06 |
| Purified water* | (29.00)* |
| Ethanol* | (5.00)* |
| Levothyroxine sodium 25 µg tablets | |
| 0.0334% levothyroxine sodium granulation intermediate | 225.00 |
| Dicalcium phosphate | 129.36 |
| Microcrystalline cellulose | 28.20 |
| FD & C yellow 6 aluminum lake | 0.39 |
| Colloidal silicon dioxide | 1.05 |
| Sodium lauryl sulfate | 0.36 |
| Magnesium stearate | 5.64 |

*removed during processing

Mannitol and levothyroxine sodium were blended for 10 minutes using conventional mixing equipment. The blended material and microcrystalline cellulose were then passed through a hammer mill and the milled materials were blended. With continuous mixing, the previously blended powders were granulated with a hydroalcoholic solution (ethanol and water) of polyvinylpyrrolidone and butylated hydroxyanisole. Additional water was added as needed for consistency of the granulation. The wet granulation mixture was dried in a fluidized bed dryer at 40° C. until the moisture content was less than 4%. The dried granulation was sized by passing it through a hammer mill then blended using conventional mixing equipment to form the 0.0334% levothyroxine sodium granulation intermediate.

Colloidal silicon dioxide, sodium lauryl sulfate, and magnesium stearate were blended and the mixture was passed through a #30 mesh screen. Microcrystalline cellulose and dicalcium phosphate were sized. The sized ingredients were then blended with the levothyroxine sodium granulation intermediate until uniform. The mixture was compressed into tablets, each weighing approximately 130 mg, on a rotary tableting machine.

EXAMPLE 2

Table 2 reports stability data for tablets made according to Example 1. The tablets were stored for 5 days at 25° C./60% RH, 40° C./75% RH and 60° C./ambient RH in a suitable pharmaceutical container. Samples of these tablets were analyzed for drug potency using a stability indicating HPLC assay method. Evaluation of the potency for these tablets (i.e., percentage label claim of levothyroxine sodium in the tablet) after five days storage demonstrates that the formulation described in Example 1, yields a product which demonstrates good stability at all temperatures at or below 60° C.

TABLE 2

Stability Data for Experiment 1

| Temperature/Relative Humidity (RH) | Tablet Potency |
|---|---|
| 25° C./60% RH | 101.8 |
| 40° C./75% RH | 98.2 |
| 60° C./Ambient RH | 95.6 |

Although the disclosure has been provided in the context of certain embodiments and examples, it will be understood by those skilled in the art that the disclosure extends beyond the specifically described embodiments to other alternative embodiments and/or uses and obvious modifications and equivalents thereof. Accordingly, the disclosure is not intended to be limited by the specific disclosures of embodiments herein.

What is claimed is:

1. A pharmaceutical composition in unit dosage form that comprises: a therapeutically effective amount of a levothyroxine sodium; an antioxidant in an amount sufficient to stabilize the levothyroxine sodium against oxidation; an amount of an alditol sufficient to stabilize the levothyroxine sodium; and at least two excipients selected from the group consisting of a filler, a binder, and a lubricant, wherein:
   the alditol is at least one member selected from the group consisting of a mannitol, a sorbitol, a maltitol, and a xylitol;
   the composition is free of added saccharide selected from the group consisting of a monosaccharide, a disaccharide, and an oligosaccharide; and
   the composition is storage stable.

2. The composition of claim 1, wherein the filler is present in the composition and is at least one member selected from the group consisting of a calcium phosphate, a cellulose, a magnesium carbonate, a calcium carbonate, and a calcium sulfate.

3. The composition of claim 1, wherein the binder is present in the composition and is at least one member selected from the group consisting of a polyvinylpyrrolidone, an alginate, a gelatin, a chitosan, a kaolin, an acacia, a methyl cellulose, a liquid glucose tragacanth, a starch, a starch paste, a pregelatinized starch, an ethyl cellulose, a hydroxypropylmethyl cellulose, a hydroxypropyl cellulose, a sodium carboxymethyl cellulose, an alginic acid, a polyvinyl pyrrolidone, a cellulose, a polyethylene glycol, a polyvinyl alcohol, and a polymethacrylate.

4. The composition of claim 1, wherein the lubricant is present in the composition and is at least one member selected from the group consisting of a talc, a calcium stearate, a sodium stearyl fumarate, a stearic acid, a magnesium stearate, a solid polyethylene glycol, a cocoa butter, a hydrogenated vegetable oil, a mineral oil, a glyceryl palmitostearate, and a glyceryl behenate.

5. The composition of claim 1, wherein the antioxidant is at least one member selected from the group consisting of a butylated hydroxyanisole, a vitamin E (alpha tocopherol), a butylated hydroxytoluene, an ascorbic acid, a sodium ascorbate, a sodium bisulfate, and a sodium metabisulfite.

6. The composition of claim 1, further comprising at least one additional excipient selected from the group consisting of a glidant and a surfactant.

7. The composition of claim 6, wherein the glidant is present in the composition and is at least one member selected from the group consisting of a talc, a silica, a fumed silica, and a colloidal silicon dioxide.

8. The composition of claim 6, wherein the surfactant is present in the composition and is at least one member selected from the group consisting of a polysorbate, a sodium lauryl sulfate, a lauryl dimethyl amine oxide, a cetyltrimethylammonium bromide, a polyethoxylated alcohol, a polyoxyethylene sorbitan, an octoxynol, a n,n-dimethyldodecylamine-n-oxide, a hexadecyltrimethylammonium bromide, a polyoxyl 10 lauryl ether, a BRIJ 721, a bile salt, a polyoxyl castor oil, a nonylphenol ethoxylate, a cyclodextrin, a lecithin, and a methylbenzethonium chloride.

9. A pharmaceutical composition in unit dosage form that comprises: a levothyroxine sodium in one amount selected from the group consisting of 25 µg, 50 µg, 75 µg, 88 µg, 100 µg, 112 µg, 137 µg, 150 µg, 175 µg, 200 µg, and 300 µg; 1%-70% w/w of an alditol; 1%-80% w/w of a filler; 0.001%-10% w/w of a binder; 0.001%-5% w/w of an antioxidant; 0.1%-5% w/w of a glidant; and 0.001%-5% w/w of a surfactant, wherein the composition is free of added saccharide selected from the group consisting of a monosaccharide, a disaccharide, and an oligosaccharide, and wherein the composition is storage stable.

10. The composition of claim 9, wherein the filler and is at least one member selected from the group consisting of a calcium phosphate, a cellulose, a magnesium carbonate, a calcium carbonate, and a calcium sulfate.

11. The composition of claim 9, wherein the binder is present in the composition and is at least one member selected from the group consisting of a polyvinylpyrrolidone, an alginate, a gelatin, a chitosan, a kaolin, an acacia, a methyl cellulose, a liquid glucose tragacanth, a starch, a starch paste, a pregelatinized starch, an ethyl cellulose, a hydroxypropylmethyl cellulose, a hydroxypropyl cellulose, a sodium carboxymethyl cellulose, an alginic acid, a polyvinyl pyrrolidone, a cellulose, a polyethylene glycol, a polyvinyl alcohol, and a polymethacrylate.

12. The composition of claim 9, wherein the lubricant is at least one member selected from the group consisting of a talc, a calcium stearate, a sodium stearyl fumarate, a stearic acid, a magnesium stearate, a solid polyethylene glycol, a cocoa butter, a hydrogenated vegetable oil, a mineral oil, a sodium lauryl sulfate, a glyceryl palmitostearate, and a glyceryl behenate.

13. The composition of claim 9, wherein the antioxidant is at least one member selected from the group consisting of a butylated hydroxyanisole, a vitamin E (alpha tocopherol), a butylated hydroxytoluene, an ascorbic acid, a sodium ascorbate, a sodium bisulfate, and a sodium metabisulfite.

14. The composition of claim 9, wherein the glidant is at least one member selected from the group consisting of a talc, a silica, a fumed silica, and a colloidal silicon dioxide.

15. The composition of claim 9, wherein the surfactant is at least one member selected from the group consisting of a polysorbate, a sodium lauryl sulfate, a lauryl dimethyl amine oxide, a cetyltrimethylammonium bromide, a polyethoxylated alcohol, a polyoxyethylene sorbitan, an octoxynol, a n,n-dimethyldodecylamine-n-oxide, a hexadecyltrimethylammonium bromide, a polyoxyl 10 lauryl ether, a BRIJ 721, a bile salt, a polyoxyl castor oil, a nonylphenol ethoxylate, a cyclodextrin, a lecithin, and a methylbenzethonium chloride.

16. A pharmaceutical composition in unit dosage form that comprises: a levothyroxine sodium in one amount selected from the group consisting of 25 μg, 50 μg, 75 μg, 88 μg, 100 μg, 112 μg, 137 μg, 150 μg, 175 μg, 200 μg, and 300 μg; 20%-60% w/w of an alditol; 10%-70% w/w of a filler; 1%-5% w/w of a binder; 0.1%-1% w/w of an antioxidant; 0.1%-3% w/w of a glidant; and 0.01%-1% w/w of a surfactant, wherein the composition is free of added saccharide selected from the group consisting of a monosaccharide, a disaccharide, and an oligosaccharide, and wherein the composition is storage stable.

17. The composition of claim 16, wherein the filler and is at least one member selected from the group consisting of a calcium phosphate, a cellulose, a magnesium carbonate, a calcium carbonate, and a calcium sulfate.

18. The composition of claim 16, wherein the binder is present in the composition and is at least one member selected from the group consisting of a polyvinylpyrrolidone, an alginate, a gelatin, a chitosan, a kaolin, an acacia, a methyl cellulose, a liquid glucose tragacanth, a starch, a starch paste, a pregelatinized starch, an ethyl cellulose, a hydroxypropylmethyl cellulose, a hydroxypropyl cellulose, a sodium carboxymethyl cellulose, an alginic acid, a polyvinyl pyrrolidone, a cellulose, a polyethylene glycol, a polyvinyl alcohol, and a polymethacrylate.

19. The composition of claim 16, wherein the lubricant is at least one member selected from the group consisting of a talc, a calcium stearate, a sodium stearyl fumarate, a stearic acid, a magnesium stearate, a solid polyethylene glycol, a cocoa butter, a hydrogenated vegetable oil, a mineral oil, a sodium lauryl sulfate, a glyceryl palmitostearate, and a glyceryl behenate.

20. The composition of claim 16, wherein the antioxidant is at least one member selected from the group consisting of a butylated hydroxyanisole, a vitamin E (alpha tocopherol), a butylated hydroxytoluene, an ascorbic acid, a sodium ascorbate, a sodium bisulfate, and a sodium metabisulfite.

21. The composition of claim 16, wherein the glidant is at least one member selected from the group consisting of a talc, a silica, a fumed silica, and a colloidal silicon dioxide.

22. The composition of claim 16, wherein the surfactant is at least one member selected from the group consisting of a polysorbate, a sodium lauryl sulfate, a lauryl dimethyl amine oxide, a cetyltrimethylammonium bromide, a polyethoxylated alcohol, a polyoxyethylene sorbitan, an octoxynol, a n,n-dimethyldodecylamine-n-oxide, a hexadecyltrimethylammonium bromide, a polyoxyl 10 lauryl ether, a BRIJ 721, a bile salt, a polyoxyl castor oil, a nonylphenol ethoxylate, a cyclodextrin, a lecithin, and a methylbenzethonium chloride.

23. A pharmaceutical composition in unit dosage form that comprises:
    a levothyroxine sodium in one amount selected from the group consisting of 25 μg, 50 μg, 75 μg, 88 μg, 100 μg, 112 μg, 137 μg, 150 μg, 175 μg, 200 μg, and 300 μg;
    37.50%-42.50% w/w of a mannitol;
    0.75%-1.50% w/w of a polyvinylpyrrolidone;
    1.00%-2.00% w/w of a magnesium stearate;
    52.50%-62.50% w/w of a microcrystalline cellulose, a dicalcium phosphate, or a combination of microcrystalline cellulose and dicalcium phosphate;
    0.20%-1.00% w/w of a colloidal silicon dioxide;
    30.00%-35.00% w/w of a dicalcium phosphate;
    0.0075%-0.015% w/w of a butylated hydroxyanisole; and
    0.075%-0.15% w/w of a sodium lauryl sulfate, and
wherein the composition is free of added saccharide selected from the group consisting of a monosaccharide, a disaccharide, and an oligosaccharide, and wherein the composition is storage stable.

\* \* \* \* \*